United States Patent [19]

Kallok et al.

[11] Patent Number: 4,499,907
[45] Date of Patent: Feb. 19, 1985

[54] ENERGY LIMITING CARDIOVERSION LEAD

[75] Inventors: Michael J. Kallok, New Brighton; Gene A. Bornzin, Coon Rapids, both of Minn.

[73] Assignee: Medtronic, Inc., Minneapolis, Minn.

[21] Appl. No.: 441,887

[22] Filed: Nov. 15, 1982

[51] Int. Cl.³ .................................. A61N 1/04
[52] U.S. Cl. .................. 128/786; 128/419 D
[58] Field of Search ........ 128/419 D, 419 P, 419 PG, 128/908, 784–786

[56] References Cited

U.S. PATENT DOCUMENTS

| | | | |
|---|---|---|---|
| 3,602,229 | 8/1971 | Jaros et al. | 128/419 D |
| 3,942,536 | 3/1976 | Mirowski | 128/419 D |
| 4,289,134 | 9/1981 | Bernstein | 128/419 PG |
| 4,320,763 | 3/1982 | Money | 128/419 PG |
| 4,355,646 | 10/1982 | Kallok et al. | 128/786 |

Primary Examiner—Lee S. Cohen
Attorney, Agent, or Firm—Reed A. Duthler; John L. Rooney; Joseph F. Breimayer

[57] ABSTRACT

A transvenous cardioversion lead for use in standby cardioversion in patients who have a high risk of ventricular tachycardia or fibrillation, adapted for use with presently available external defibrillation units. The lead is provided with energy-reducing or energy-limiting circuitry to prevent the inappropriately high energy levels which may be generated by external defibrillation units from causing injury to the patient while preserving the beneficial waveform of the defibrillation pulse. The lead is further provided with at least three electrodes, two for location in the ventricle, at least one for location in the superior vena cava. The lead is so constructed that the superior vena cava electrode and one of the ventricular electrodes may be used for cardioversion, while the two ventricular electrodes may be used for cardiac pacing and sensing.

12 Claims, 3 Drawing Figures

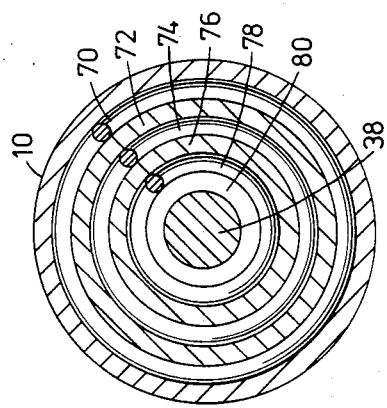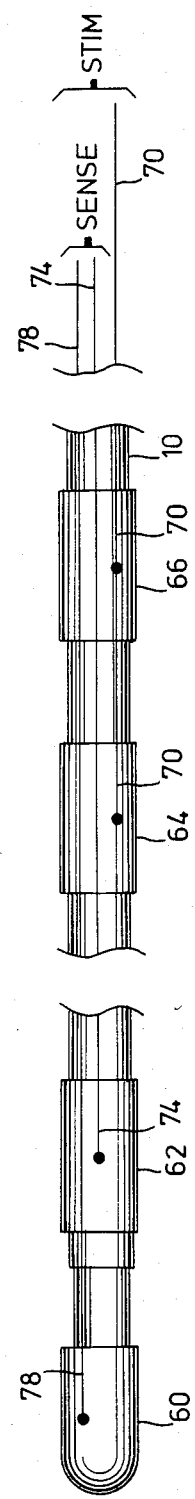

ENERGY LIMITING CARDIOVERSION LEAD

BACKGROUND OF THE INVENTION

1. Field of the Invention

The present invention relates generally to electrical medical leads, and more specfically relates to transvenous cardioversion leads. For purposes of this application, "cardioversion" is used in its broad sense, as including defibrillation and termination of tachycardias.

2. Description of the Prior Art

Research to provide an automatic implantable standby cardioverter has been in progress for over ten years. One result of this research has been the development of transvenous cardioversion leads. The primary perceived advantage of a transvenous lead used in conjunction with an implantable cardioverter is that the energy required for cardioversion by this method is significantly reduced, making an implantable defibrillator feasible.

Mirowski, et al in U.S. Pat. No. 3,942,536 teaches an early defibrillation lead. The lead is provided with multiple electrodes for location at the apex of the right ventricle and multiple electrodes for location in the superior vena cava.

Rubin, in U.S. Pat. No. 3,857,398 teaches a transvenous defibrillation lead having a first electrode at the tip of the lead for location in the ventricular apex, a second electrode slightly proximal to the first electrode for location in the ventricle, and a third electrode for location in the right atrium. The first and second electrodes are used for cardiac pacing while the first and third electrodes are used for defibrillation.

In addition to benefiting the designers of implantable cardioverters, the lower energy levels associated with transvenous caradioversion also benefit the patient. As noted in the Mirowski patent referenced above, transvenous defibrillation has several medical advantages over external defibrillation as presently practiced. First, high energy transthoracic defibrillation generally results in extreme pain, often necessitating the use of general anesthetic. Second, because of the high energy levels involved, transthoracic defibrillation poses a substantial risk of cardiac damage. Both of these problems can be reduced by the precise localization of defibrillation energy allowed by the use of a transvenous defibrillation lead.

The leads disclosed by Rubin, Mirowski and others are suitable for use with low-energy standby defibrillators which, typically, generate only a fraction of the energy produced by standard external defibrillation units. However, at present, such low-energy standby defibrillators are not widely available. Use of a lead as disclosed by Rubin or Mirowski with an external defibrillation unit is impractical. First, a lead as disclosed by Rubin or Mirowski is a direct, low-impedance electrical pathway to the heart. Connection of such a lead to an external defibrillation unit poses a significant risk of injury to the patient. Typical external defibrillation units are capable of delivering up to 400 joules of energy, and any missetting or malfunction of such a device connected to a transvenous lead according to the prior art poses a significant risk of injury or death. Second, the external unit is provided with a scale which typically reads from 0 to 400 joules while transvenous defibrillation generally requires less than 40 joules and termination of tachycardias generally requires less than 2 joules. Any adjustment of the external unit must therefore take place within the lower 10% of the scale, making accurate setting of energy levels extremely difficult. Finally, external defibrillation devices are generally designed to deliver pulses across a nominal load of 50 ohms, while the typical transvenous lead exhibits a nominal load of approximately 100 ohms.

SUMMARY OF THE INVENTION

The present invention is a transvenous cardioversion lead which may safely and effectively be used in conjunction with an external defibrillation unit for transvenous cardioversion of the human heart. This lead allows physicians to obtain the benefits of transvenous cardioversion without the necessity of procuring a low-energy standby cardioversion or defibrillation unit. The lead is so designed to avoid the problems cited above which prevent the use of prior art leads with external defibrillation units. First, the lead is provided with circuitry which reduces energy from the defibrillator to a safe level for use with transvenous defibrillation. Second, in its preferred embodiment, the circuitry reduces the energy level applied to the heart to a fixed 10% of the energy level generated by the external defibrillation unit, allowing use of the whole scale of the external defibrillation unit, and thereby facilitating accurate adjustment of defibrillation energy applied to the heart. Third, the lead is designed to present a nominal load, as implanted, of 50 ohms. By presenting the defibrillation unit with the appropriate load, preservation of the beneficial wave shape of the defibrillation pulse is accomplished. Finally, the circuitry is so designed that it allows the use of the two ventricular electrodes for cardiac pacing, making the lead suitable for use with external temporary pacemakers.

BRIEF DESCRIPTION OF THE DRAWINGS

FIG. 2 illustrates a cross-section of the lead shown in FIG. 1, showing the arrangement of the conductors;

FIG. 3 is a schematic diagram showing the electrical coupling of the electrodes to the conductors within the lead body;

DETAILED DESCRIPTION OF THE PREFERRED EMBODIMENTS

Figure 1:
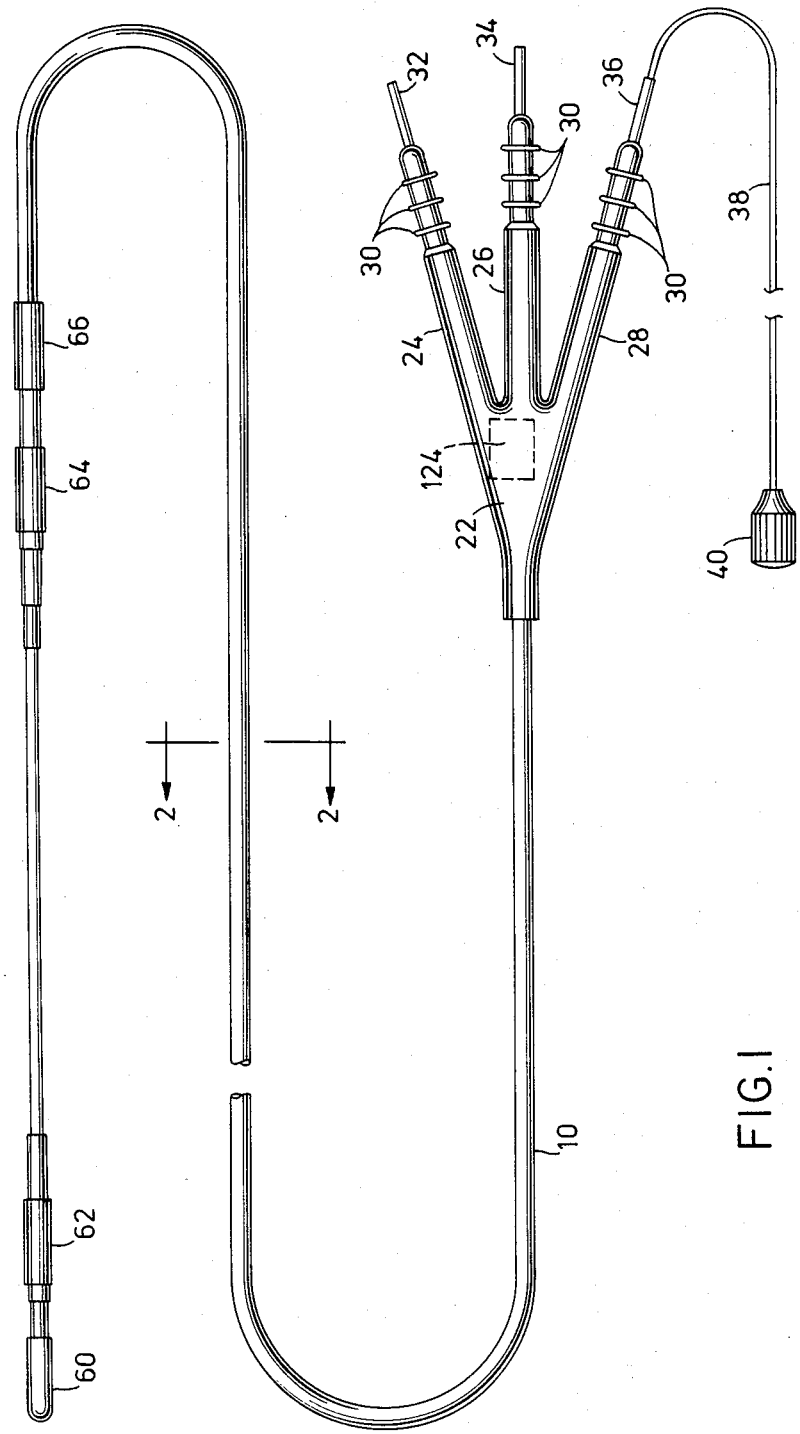
FIG. 1 illustrates a plan view of a lead according to the present invention.

FIG. 1 shows a transvenous cardioversion lead employing the present invention. The lead has four electrodes. Electrodes 60 and 62 are the distal electrodes which are positioned within the right ventricle. Proximal electrodes 64 and 66 are connected in common and are positioned within the superior vena cava. All four electrodes may be fabricated of any conductor which is essentially inert to body fluids. The preferred mode employs stainless steel, however, other materials such as titanium or platinum and its alloys may be used. The main body of the lead is covered with a polyurethane sheath 10. Connector 22 is provided with three furcations 24, 26 and 28, each of which is provided with a connector pin 32, 34, and 36 respectively. Each of the furcations is provided with three sealing rings 30. Stylet wire 38 having a knob 40 at its distal end may be inserted into terminal pin 36 and extended through lumen 80 (not illustrated) until it reaches distal electrode 60. A stylet is used for guiding the lead during transvenous implantation.

Located within connector assembly 22 is circuitry 124, illustrated by broken line. Two embodiments of circuitry 124 are illustrated in FIGS. 4 and 5 below.

FIG. 2 is a cross-section of the main lead body. Outer sheath 10 protects the lead from ingress of body fluids. Conductors 70, 74, and 78 are mounted coaxially within the lead. Each is a quadrifilar helical coil of drawn brazed strand (DBS TM) wire. The three conductors are mutually insulated by polyurethane sheaths 72 and 76. Lumen 80 is visible in cross-section containing stylet 38. FIG. 3 illustrates schematically the electrical connections of the electrodes of the lead illustrated in FIGS. 1 and 2. Conductor 78 is electrically connected to electrode 60. Conductor 74, which is the middle conductor in the coaxial configuration, is connected electrically to electrode 62. Conductor 78, which is the outer conductor, is connected electrically to both electrodes 64 and 66. Electrodes 64 and 66 are thus the electrical equivalent of a single electrode. This arrangement of electrodes allows electrodes 60 and 62 to be used for sensing heart activity and for cardiac pacing if desired. Electrode 60 may be coupled to electrode 62 by connecting pins 34 and 36 in common, for use in cardioversion. This is especially valuable in defibrillation applications, which employ higher energy levels.

Figure 4:
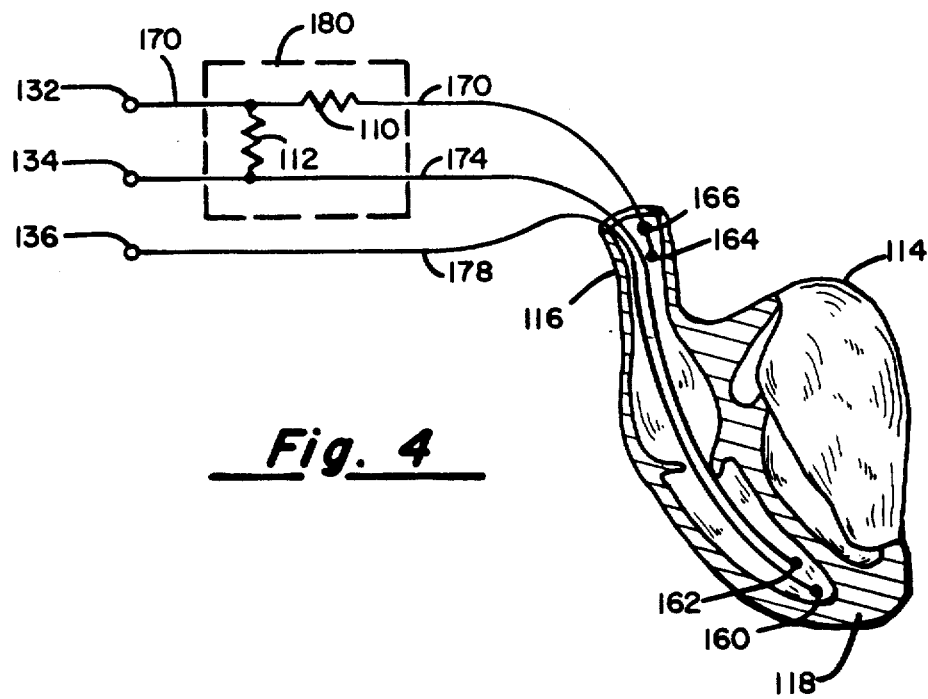
FIG. 4 is a schematic diagram of the first embodiment of the present invention, showing the circuitry within the lead and its relationship to the heart.

FIG. 4 illustrates schematically the circuitry of a first embodiment of the lead and its relationship to the heart as implanted. Conductor 170, 174 and 178 correspond to conductors 70, 74 and 78 as illustrated in FIGS. 2 and 3. Electrodes 160, 162, 164 and 166 correspond to electrodes 60, 62, 64 and 66 respectively illustrated in FIGS. 2 and 3. Similarly, connector pins 132, 134 and 136 correspond to connectors pins 32, 34 and 36. Energy-reducing circuitry 183, enclosed by a broken line, corresponds to circuitry 124 (FIG. 1). Energy-limiting circuitry 180 consists of a first resistor 112 bridging conductors 170 and 174 and a second resistor 110 located in-line with conductor 170. Appropriate values for resistors 110 and 112 are 123 ohms and 64 ohms respectively, which result in a 90% reduction in energy delivered between electrodes 160 and 164 as compared with energy applied to connector pins 132 and 134. It is important to note that, by constructing energy-reducing circuitry 180 in this fashion, conductors 134 and 136 may be utilized for transvenous pacing and sensing with a standard external pacemaker. As such, the lead may be implanted for use with a temporary pacemaker, while being available for use as a defibrillation lead if the need should arise.

Figure 5:
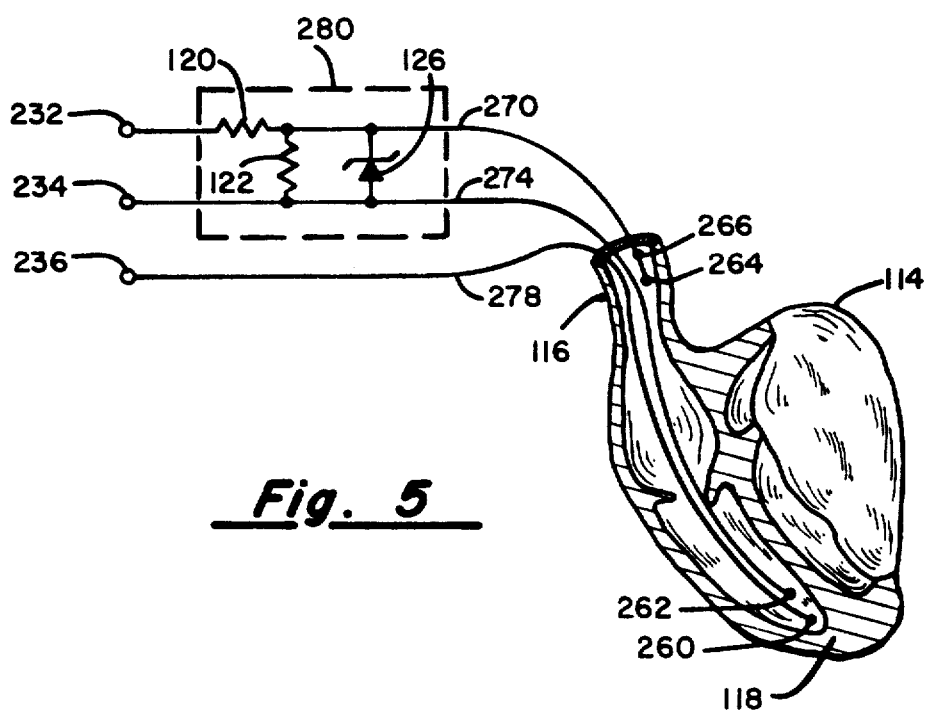
FIG. 5 is a schematic diagram of a second embodiment of the present invention showing the circuitry within the lead and its relationship to the heart.

FIG. 5 illustrates schematically the circuitry of a second embodiment of the defibrillation lead and its relationship to the heart as implanted. Conductors 270, 274 and 278 corresponds to conductors 70, 74 and 78 illustrated in FIGS. 2 and 3. Electrodes 260, 262, 264 and 266 correspond to electrodes 60, 62, 64 and 66 illustrated in FIGS. 2 and 3. Similarly, connector pins 232, 234 and 236 correspond to connector pins 32, 34 and 36 illustrated in FIGS. 2 and 3. Energy-reducing and limiting circuitry 280, illustrated by a broken line corresponds to circuitry 124 (FIG. 1). Energy-limiting and reducing circuitry 280 consists of a first resistor 122 bridging conductors 270 and 274 and a second resistor 120 in-line with conductor 270. An appropriate value for both resistors 120 and 122 is 28 ohms. Also bridging conductors 270 and 274 is zener diode 126, which acts as an energy-limiting means, due to its nonlinear conductor characteristics. Resistors 120 and 122 reduce energy applied across electrodes 260 and 264 to 10% of the energy applied across connector pins 232 and 234. Because of zener diode 126, the polarity of connection to the external defibrillation unit is important. Connector 234 should be connected to the ground potential. So connected, the lead supplies an impedance of approximately 50 ohms. In the presence of excessively high energy levels, zener diode 126 will conduct energy applied at connector 232 to connector 234, shunting current away from the heart, preventing damage to the patient. By selecting a suitable value for zener diode 126, the maximum energy level which may be applied to the heart can be selected. This lead, like the lead of FIG. 4 may also be used for cardiac pacing and sensing by connecting connector pins 234 and 236 to a standard external temporary pacemaker. The lead may later be used for transvenous defibrillation if the need arises.

Having thus described the preferred mode of the present invention, those of ordinary skill in the art will recognize that certain of the design characteristics taught herein may be varied and still remain within the scope of the present invention.

What is claimed is:

1. A transvenous cardioversion lead for implant in the human heart, comprising:
   an elongated insulative lead body;
   a first conductor, having a proximal end and a distal end, mounted within said lead body;
   a second conductor, having a proximal and a distal end, mounted within said lead body, insulated from said first conductor;
   a first connector, coupled to the proximal end of said first conductor;
   a second connector, coupled to the proximal end of said second conductor;
   a first electrode, exposed to the exterior of said lead body and coupled to the distal end of said first conductor, for applying electrical energy to heart tissue;
   a second electrode, exposed to the exterior of said lead body and coupled to the distal end of said second conductor, for applying electrical energy to heart tissue; and
   energy-reducing means coupled to said first and second conductors for reducing the electrical energy of a cardioversion pulse applied to said first and second connectors from a first energy as applied to said first and second connectors to a reduced second energy as applied to said heart tissue by said first and second electrodes.

2. A transvenous cardioversion lead according to claim 1 wherein said second energy varies with said first energy and is a fixed percentage of said first energy.

3. A transvenous cardioversion lead according to claim 2 wherein said fixed percentage is 10%.

4. A transvenous cardioversion lead according to claim 1 or claim 2 or claim 3 wherein said energy-reducing means reduces the electrical energy of said cardioversion pulse by reducing the amplitude of said cardioversion pulse and the current associated with said cardioversion pulse while retaining the pulse width of said cardioversion pulse and preserving the basic wave form of said cardioversion pulse.

5. A transvenous cardioversion lead according to claim 1 or claim 2 or claim 3 further comprising energy-limiting means coupled to said first and second conductors for preventing said second energy from exceeding a maximum energy level.

6. A transvenous cardioversion lead for implantation in the human heart, comprising:
an elongated insulative lead body;
a first conductor, having a proximal end and a distal end, mounted within said lead body;
a second conductor, having a proximal end and a distal end, mounted within said lead body, insulated from said first conductor;
a first connector coupled to the proximal end of said first conductor;
a second connector coupled to the proximal end of said second conductor;
a first electrode exposed to the exterior of said lead body and coupled to the distal end of said first conductor for applying electrical energy to heart tissue;
a second electrode exposed to the exterior of said lead body and coupled to the distal end of said second conductor for applying electrical energy to heart tissue; and
energy-limiting means coupled to said first and second conductors for passing the electrical energy of a cardioversion pulse applied to said first and second connectors to said first and second electrodes only up to a maximum energy level, and preventing the energy of said cardioversion pulse from being applied to said heart tissue in excess of said maximum energy level.

7. A transvenous cardioversion lead for implant in the human heart, comprising:
an elongated insulative lead body;
a first conductor, having a proximal end and a distal end, mounted in said lead body;
a second conductor, having a proximal end and a distal end, mounted within said lead body, insulated from said first conductor;
a third conductor, having a proximal end and a distal end, mounted within said lead body, insulated from said first and second conductors;
a first connector, coupled to the proximal end of said first conductor;
a second connector, coupled to the proximal end of said second conductor;
a third connector, coupled to the proximal end of said third conductor;
a first electrode, exposed to the exterior of said lead body and coupled to the distal end of said first conductor for applying electrical energy to heart tissue;
a second electrode exposed to the exterior of said lead body and coupled to the distal end of said second conductor for applying electrical energy to heart tissue;
a third electrode exposed to the exterior of said lead body and coupled to the distal end of said second conductor for applying electrical energy to heart tissue; and
energy-reducing means coupled to said first and second conductors for reducing the electrical energy of a cardioversion pulse applied to said first and second connectors to a reduced second energy as applied to said heart tissue by said first and second electrodes, while passing the electrical energy of a pacing pulse applied to said second and third connectors substantially undiminished to said second and third electrodes for application to said heart tissue.

8. A transvenous cardioversion lead according to claim 7 wherein said second energy varies with, and is a fixed percentage of, said first energy.

9. A transvenous cardioversion lead according to claim 8 wherein said fixed percentage is 10%.

10. A transvenous cardioversion lead according to claim 7 or claim 8 or claim 9 wherein said energy-reducing means reduces the electrical energy of a cardioversion pulse by reducing the amplitude of said cardioversion pulse and the current associated with said cardioversion pulse while retaining the pulse width of said cardioversion pulse and preserving the basic wave form of said cardioversion pulse.

11. A transvenous cardioversion lead according to claim 7 or claim 8 or claim 9 further comprising energy-limiting means coupled to said first and second conductors for preventing said second energy from exceeding a maximum energy level.

12. A transvenous cardioversion lead for implantation in the human heart, comprising:
an elongated insulative lead body;
a first conductor having a proximal end and a distal end, mounted within said lead body;
a second conductor having a proximal end and a distal end, mounted within said lead body, insulated from said first conductor;
a third conductor having a proximal end and distal end, mounted within said lead body, insulated from said first and second conductors;
a first connector coupled to the proximal end of said first conductor;
a second connector coupled to the proximal end of said second conductor;
a third connector coupled to the proximal end of said third conductor;
a first electrode exposed to the exterior of said lead body and coupled to the distal end of said first conductor, for applying electrical energy to heart tissue;
a second electrode exposed to the exterior of said lead body and coupled to the distal end of said second conductor for applying electrical energy to heart tissue;
a third electrode exposed to the exterior of said lead body and coupled to the distal end of said third conductor for applying electrical energy to heart tissue; and
energy-limiting means coupled to said first and second conductors for passing the electrical energy of a cardioversion pulse applied to said first and second connectors to said first and second electrodes only up to a maximum energy level, preventing the energy of said cardioversion pulse from being applied to said heart tissue in excess of said maximum energy level.

* * * * *

UNITED STATES PATENT AND TRADEMARK OFFICE
CERTIFICATE OF CORRECTION

PATENT NO. : 4,499,907
DATED : February 19, 1985
INVENTOR(S) : Michael J. Kallok It is certified that error appears in the above-identified patent and that said Letters Patent is hereby corrected as shown below:

The sheet of drawings consisting of Figs. 4 and 5 should be added as shown on the attached sheets.

On the title page, "12 Claims, 3 Drawing Figures" should read -- 12 Claims, 5 Drawing Figures --.

Signed and Sealed this

Nineteenth Day of November 1985

[SEAL]

Attest:

DONALD J. QUIGG

Attesting Officer

Commissioner of Patents and Trademarks